United States Patent
Palaio

(10) Patent No.: US 12,214,069 B2
(45) Date of Patent: Feb. 4, 2025

(54) HEMP-BASED COSMECEUTICAL COMPOSITIONS AND METHODS OF MAKING SAME

(71) Applicant: NP Pharma Holdings, LLC, Sheridan, WY (US)

(72) Inventor: Peyton Palaio, Cumming, GA (US)

(73) Assignee: NP Pharma, LLC, Sheridan, WY (US)

( * ) Notice: Subject to any disclaimer, the term of this patent is extended or adjusted under 35 U.S.C. 154(b) by 0 days.

(21) Appl. No.: 16/879,639

(22) Filed: May 20, 2020

(65) Prior Publication Data

US 2020/0375882 A1    Dec. 3, 2020

Related U.S. Application Data

(60) Provisional application No. 62/854,173, filed on May 29, 2019.

(51) Int. Cl.

| | | |
|---|---|---|
| *A61K 8/9789* | (2017.01) | |
| *A61K 8/33* | (2006.01) | |
| *A61K 8/73* | (2006.01) | |
| *A61Q 1/02* | (2006.01) | |
| *A61Q 1/04* | (2006.01) | |
| *A61Q 1/06* | (2006.01) | |
| *A61Q 1/08* | (2006.01) | |
| *A61Q 1/10* | (2006.01) | |
| *A61Q 1/12* | (2006.01) | |
| *A61Q 17/04* | (2006.01) | |
| *A61Q 19/00* | (2006.01) | |
| *A61Q 19/10* | (2006.01) | |
| *C08L 1/02* | (2006.01) | |

(52) U.S. Cl.
CPC .............. *A61K 8/9789* (2017.08); *A61K 8/33* (2013.01); *A61K 8/731* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 1/12* (2013.01); *A61Q 17/04* (2013.01); *A61Q 19/007* (2013.01); *A61Q 19/10* (2013.01); *C08L 1/02* (2013.01)

(58) Field of Classification Search
None
See application file for complete search history.

(56) References Cited

U.S. PATENT DOCUMENTS

| | | |
|---|---|---|
| 5,123,962 A | 6/1992 | Komuro et al. |
| 9,388,343 B2 | 7/2016 | Rehage |
| 2004/0161524 A1 | 8/2004 | Sakai et al. |
| 2004/0192760 A1 | 9/2004 | Whittle et al. |
| 2007/0122492 A1 | 5/2007 | Behr et al. |
| 2007/0141017 A1 | 6/2007 | Horska |
| 2010/0074879 A1* | 3/2010 | Aoki ................ A61P 43/00 424/94.1 |
| 2011/0223223 A1 | 9/2011 | Murata et al. |
| 2015/0247009 A1 | 9/2015 | Mitchell |
| 2016/0324908 A1* | 11/2016 | Bates ............... A61K 36/185 |
| 2017/0020814 A1 | 1/2017 | Benson et al. |
| 2017/0071214 A1 | 3/2017 | Rehage |
| 2018/0193403 A1 | 7/2018 | George et al. |

FOREIGN PATENT DOCUMENTS

| | | | |
|---|---|---|---|
| CA | 3054256 | | 10/2018 |
| CN | 101787571 | * | 7/2010 |
| CN | 102274140 B | | 2/2013 |
| CN | 109267157 A | | 1/2019 |
| FR | 2014/0145057 | * | 9/2014 |
| JP | 2000327519 A | | 11/2000 |
| KR | 101840130 B1 | | 3/2018 |
| WO | WO 2018/178121 | | 10/2018 |

OTHER PUBLICATIONS

Zhang et al., Transparent Ultraviolet (UV)-Shielding Films Made from Waste Hemp Hurd and Polyvinyl Alcohol (PVA), Polymers 2020, 12, 1190. (Year: 2020).*

International Search Report and Written Opinion mailed on Aug. 7, 2020 by the International Searching Authority for International Application No. PCT/US2020/034931, filed on May 28, 2020 (Applicant—Precision Biologics) (10 pages).

* cited by examiner

*Primary Examiner* — David J Blanchard
*Assistant Examiner* — Sarah J Chickos
(74) *Attorney, Agent, or Firm* — Ballard Spahr LLP

(57) ABSTRACT

Provided are cosmeceutical composition comprising a hemp base and methods of making such cosmeceutical compositions. The hemp base can be prepared, for example, by micronizing a hemp flour and isolating the resultant particles based on their size. This abstract is intended as a scanning tool for purposes of searching in the particular art and is not intended to be limiting of the present invention.

20 Claims, No Drawings

HEMP-BASED COSMECEUTICAL COMPOSITIONS AND METHODS OF MAKING SAME

CROSS-REFERENCE TO RELATED APPLICATIONS

This Application claims the benefit of U.S. Application No. 62/854,173, filed on May 29, 2019, the contents of which are hereby incorporated by reference in their entirety.

BACKGROUND

Cosmeceutical compositions are used to provide various benefits and to meet different consumer needs. These needs can include, for example, functional benefits such as skin moisturizing, wrinkle reduction, skin whitening, and the like. Consumer needs can also include desirable consumer use experiences such as, for example, pleasant smell, smooth texture, appealing color, and overall appearance of the composition.

The hemp plant and, more specifically, particles derived from the hemp plant, offer unique properties that appear to make them desirable for incorporation into cosmetic compositions. For example, these particles have unique electronic properties, which make them more complementary to cosmetic products than cow-based or cow substitute-based materials. Moreover, the general charge of the particles can be modified based on how the powder is processed subsequent to removal of the hemp chemicals. In addition, particles derived from a hemp plant have an excellent toxicity profile. This is a substantial benefit over conventional talc products.

Despite these beneficial properties, however, the incorporation of hemp-based particles into cosmeceutical compositions has yet to be explored. Thus, there remains a need for hemp-based cosmeceutical compositions and methods of making and using same. These needs and others are met by the present invention.

SUMMARY

In accordance with the purpose(s) of the invention, as embodied and broadly described herein, the invention, in one aspect, relates to hemp-based cosmeceutical compositions and methods of making same.

Thus, disclosed are cosmeceutical compositions comprising a hemp base, wherein the hemp base comprises a plurality of particles and wherein the hemp base is substantially free of oil.

Also disclosed are cosmeceutical compositions comprising a hemp base, wherein the hemp base has a plurality of particles within a particle size range and wherein the hemp base was produced by: (a) micronizing a hemp flour consisting essentially of a hemp hurd or a hemp seed shell, thereby providing a particulate hemp composition; and (b) isolating the plurality of particles based on the particle size range.

Also disclosed are cosmeceutical compositions comprising a hemp base, wherein the hemp base has a plurality of particles within a particle size range and wherein the hemp base was produced by: (a) extracting from a hemp composition consisting essentially of a hemp flower, thereby providing a hemp flour; (b) micronizing the hemp flour, thereby providing a particulate hemp composition; and (c) isolating the plurality of particles based on the particle size range.

Also disclosed are cosmeceutical compositions comprising a hemp base, wherein the hemp base has a plurality of particles within a particle size range and wherein the hemp base was produced by: (a) de-gumming a hemp composition consisting essentially of a hemp fiber, thereby providing a hemp flour; (b) micronizing the hemp flour, thereby providing a particulate hemp composition; and (c) isolating the plurality of particles based on the particle size range.

Also disclosed are methods for making a hemp base having a plurality of particles within a particle size range, the method comprising: (a) micronizing a hemp flour consisting essentially of a hemp hurd or a hemp seed shell, thereby providing a particulate hemp composition; and (b) isolating the plurality of particles based on the particle size range, thereby producing the hemp base.

Also disclosed are methods for making a hemp base having a plurality of particles within a particle size range, the method comprising: (a) extracting from a hemp composition consisting essentially of a hemp flower, thereby producing a hemp flour comprising cellulose and lignin; (b) micronizing the hemp flour to provide a particulate hemp composition; and (c) isolating the plurality of particles based on the particle size range, thereby producing the hemp base.

Also disclosed are methods for making a hemp base having a plurality of particles within a particle size range, the method comprising: (a) de-gumming a hemp composition consisting essentially of a hemp fiber, thereby producing a hemp flour comprising cellulose and lignin; (b) micronizing the hemp flour to provide a particulate hemp composition; and (c) isolating the plurality of particles based on the particle size range, thereby producing the hemp base.

Still other objects and advantages of the present disclosure will become readily apparent by those skilled in the art from the following detailed description, wherein it is shown and described only the preferred aspects, simply by way of illustration of the best mode. As will be realized, the disclosure is capable of other and different aspects, and its several details are capable of modifications in various obvious respects, without departing from the disclosure. Accordingly, the description is to be regarded as illustrative in nature and not as restrictive.

DETAILED DESCRIPTION

The present invention can be understood more readily by reference to the following detailed description of the invention and the Examples included therein.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present compositions, methods and systems may be understood more readily by reference to the following detailed description of preferred embodiments and the examples included therein and to the Figures and their previous and following description.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and in the claims, the term "comprising" can include the aspects "consisting of" and "consisting essentially of".

As used in the specification and the appended claims, the singular forms "a," "an," and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

"Optional" or "optionally" means that the subsequently described event or circumstance may or may not occur, and that the description includes instances where said event or circumstance occurs and instances where it does not.

As used herein, the term "by weight," when used in conjunction with a component, unless specially stated to the contrary is based on the total weight of the formulation or composition in which the component is included. For example, if a particular element or component in a composition or article is said to have 8% by weight, it is understood that this percentage is in relation to a total compositional percentage of 100%.

A weight percent of a component, or weight %, or wt %, unless specifically stated to the contrary, is based on the total weight of the formulation or composition in which the component is included.

References in the specification and concluding claims to parts by weight of a particular element or component in a composition or article, denotes the weight relationship between the element or component and any other elements or components in the composition or article for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

As used herein, the term "substantially," in, for example, the context "substantially free" refers to a composition having less than about 10% by weight, e.g., less than about 5%, less than about 1%, less than about 0.5% by weight, less than about 0.1% by weight, less than about 0.05% by weight, or less than about 0.01% by weight of the stated material, based on the total weight of the composition.

It is further understood that the term "substantially," when used in reference to a composition, refers to at least about 60% by weight, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature, component, or a combination of the components. It is further understood that if the composition comprises more than one component, the two or more components can be present in any ratio predetermined by one of ordinary skill in the art.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

Disclosed are also components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

B. Cosmeceutical Compositions

In one aspect, disclosed are cosmeceutical compositions comprising a hemp base, wherein the hemp base comprises a plurality of particles and wherein the hemp base is substantially free of oil.

In one aspect, disclosed are cosmeceutical composition comprising a hemp base, wherein the hemp base has a plurality of particles within a particle size range and wherein the hemp base was produced by: (a) micronizing a hemp flour consisting essentially of a hemp hurd or a hemp seed shell, thereby providing a particulate hemp composition; and (b) isolating the plurality of particles based on the particle size range.

In one aspect, disclosed are cosmeceutical compositions comprising a hemp base, wherein the hemp base has a plurality of particles within a particle size range and wherein the hemp base was produced by: (a) extracting from a hemp composition consisting essentially of a hemp flower, thereby providing a hemp flour; (b) micronizing the hemp flour, thereby providing a particulate hemp composition; and (c) isolating the plurality of particles based on the particle size range.

In one aspect, disclosed are cosmeceutical compositions comprising a hemp base, wherein the hemp base has a plurality of particles within a particle size range and wherein the hemp base was produced by: (a) de-gumming a hemp composition consisting essentially of a hemp fiber, thereby providing a hemp flour; (b) micronizing the hemp flour, thereby providing a particulate hemp composition; and (c) isolating the plurality of particles based on the particle size range.

In various aspects, the composition is topical.

In various aspects, compositions of the present invention can be in any form suitable for topical use such as, for example, an aerosol, cream, ointment, lotion, dusting powder, gel, jelly, and the like. These formulations can be prepared via conventional processing methods known to one skilled in the art.

In a further aspect, the composition is an ointment, a gel, a jelly, an oil, a cream, a paste, an aerosol foam, an aerosol spray, a lotion, or a powder. In a still further aspect, the composition is a cream. In yet a further aspect, the composition is a powder.

In a further aspect, the composition further comprises an additive. Examples of additives include, but are not limited to, a colorant, an emollient, a flavorant, a fragrant, a sunscreen, a self-tanning agent, an opacifying agent, a moisturizer, a film former, a thickening agent, a conditioning agent, a deodorant, an emulsifier, a humectant, a softener, a lubricant, a penetrant, a plastisizer, a dispersant, a preservative, and mixtures thereof In a further aspect, the additive is present in an amount of from about 0.01 wt % to about 10 wt % of the composition. In a still further aspect, the additive is present in an amount of from about 0.01 wt % to about 8 wt % of the composition. In yet a further aspect, the additive is present in an amount of from about 0.01 wt % to about 6 wt % of the composition. In an even further aspect, the additive is present in an amount of from about 0.01 wt % to about 4 wt % of the composition. In a still further aspect, the additive is present in an amount of from about 0.01 wt % to about 2 wt % of the composition. In yet a further aspect, the additive is present in an amount of from about 0.01 wt % to about 1 wt % of the composition. In an even further aspect, the additive is present in an amount of from about 0.1 wt % to about 10 wt % of the composition. In a still further aspect, the additive is present in an amount of from about 1 wt % to about 10 wt % of the composition. In yet a further aspect, the additive is present in an amount of from about 2 wt % to about 10 wt % of the composition. In an even further aspect, the additive is present in an amount of from about 4 wt % to about 10 wt % of the composition. In a still further aspect, the additive is present in an amount of from about 6 wt % to about 10 wt % of the composition. In yet a further aspect, the additive is present in an amount of from about 8 wt % to about 10 wt % of the composition.

It is understood that the disclosed compositions can be employed in the disclosed methods of using.

1. Hemp Base

In one aspect, the disclosed cosmeceutical compositions comprise a hemp base.

In various aspects, the hemp base is substantially free of oil.

In various aspects, the hemp base comprises less than about 10 wt % oil. In a further aspect, the hemp base comprises less than about 9 wt % oil. In a still further aspect, the hemp base comprises less than about 8 wt % oil. In yet a further aspect, the hemp base comprises less than about 7 wt % oil. In an even further aspect, the hemp base comprises less than about 6 wt % oil. In a still further aspect, the hemp base comprises less than about 5 wt % oil. In yet a further aspect, the hemp base comprises less than about 4 wt % oil. In an even further aspect, the hemp base comprises less than about 3 wt % oil. In a still further aspect, the hemp base comprises less than about 2 wt % oil. In yet a further aspect, the hemp base comprises less than about 1 wt % oil. In an even further aspect, the hemp base comprises less than about 0.5 wt % oil. In a still further aspect, the hemp base comprises less than about 0.1 wt % oil. In yet a further aspect, the hemp base comprises less than about 0.05 wt % oil. In an even further aspect, the hemp base comprises less than about 0.01 wt % oil.

Without wishing to be bound by theory, the manner in which the hemp base is produced may be dependent on the material component of the hemp plant or *Cannabis sativa* utilized. The hemp plant of *Cannabis sativa* is a species of the Cannabis family typically found in the northern hemisphere. The material components of the plant can be separated into four respective components: the fiber/bast fiber; the hurd; the flower; and the seed.

Both the fiber and the hurd originate from the stalk. All stalk material must first be decorticated—separating the outer bast fiber (i.e., the outer portion of the stalk) from the inner hurd (i.e., the woody core) of the plant. The fiber must then be de-gummed before being micronized to the desired particle size range. In contrast, the hurd can be micronized directly.

The flower must be extracted and removed of the resinous, fatty, waxy, phtyo-chemical, or cannabinoid components. Once these components have been removed, the material can then be micronized.

Finally, the seed can be separated into the shell and the "heart" or meat of the hemp seed (e.g., via mechanical means). The shell of the seed can then be micronized to the desired particle size range. Such material may be useful, for example, as an abrasive or exfoliating component.

Thus, in various aspects, the hemp base was produced via micronizing a hemp flour. In a further aspect, the hemp flour consists essentially of a hemp hurd or a hemp seed shell. Thus, in various aspects, the hemp flour comprises the hemp hurd and/or the hemp seed shell in an amount of at least about 75 wt %, at least about 80 wt %, at least about 85 wt %, at least about 90 wt %, at least about 95 wt %, at least about 99 wt %, or greater than about 99 wt %.

In a further aspect, the hemp flour was produced via extraction a hemp composition. In a still further aspect, the hemp composition consists essentially of a hemp flour. Thus, in various aspects, the hemp composition comprises the hemp flour in an amount of at least about 75 wt %, at least about 80 wt %, at least about 85 wt %, at least about 90 wt %, at least about 95 wt %, at least about 99 wt %, or greater than about 99 wt %. In yet a further aspect, de-gumming is enzymatic de-gumming.

In yet a further aspect, the hemp composition is substantially free of cannabinoids. Thus, in various aspects, the hemp composition comprises less than about 10 wt % cannabinoids. In a further aspect, the hemp composition comprises less than about 9 wt % cannabinoids. In a still further aspect, the hemp composition comprises less than about 8 wt % cannabinoids. In yet a further aspect, the hemp composition comprises less than about 7 wt % cannabinoids. In an even further aspect, the hemp composition comprises less than about 6 wt % cannabinoids. In a still further aspect, the hemp composition comprises less than about 5 wt % cannabinoids. In yet a further aspect, the hemp composition comprises less than about 4 wt % cannabinoids. In an even further aspect, the hemp composition comprises less than about 3 wt % cannabinoids. In a still further aspect, the hemp composition comprises less than about 2 wt % cannabinoids. In yet a further aspect, the hemp composition comprises less than about 1 wt % cannabinoids. In an even further aspect, the hemp composition comprises less than about 0.5 wt % cannabinoids. In a still further aspect, the hemp composition comprises less than about 0.1 wt % cannabinoids. In yet a further aspect, the hemp composition comprises less than about 0.05 wt % cannabinoids. In an even further aspect, the hemp composition comprises less than about 0.01 wt % cannabinoids.

In a further aspect, the hemp flour was produced via de-gumming a hemp composition. In a still further aspect, the hemp composition consists essentially of a hemp fiber. Thus, in various aspects, the hemp composition comprises the hemp fiber in an amount of at least about 75 wt %, at least about 80 wt %, at least about 85 wt %, at least about 90 wt %, at least about 95 wt %, at least about 99 wt %, or greater than about 99 wt %. In yet a further aspect, de-gumming is enzymatic de-gumming.

In various aspects, the hemp base consists essentially of cellulose and lignin. Thus, in various aspects, the hemp base comprises the cellulose and/or lignin in an amount of at least about 75 wt %, at least about 80 wt %, at least about 85 wt %, at least about 90 wt %, at least about 95 wt %, at least about 99 wt %, or greater than about 99 wt %.

In various aspects, the hemp base is present in an amount of from about 5 wt % to about 98 wt %, based on the total weight of the composition. In an even further aspect, the hemp base is present in an amount of from about 5 wt % to about 90 wt %, based on the total weight of the composition. In a further aspect, the hemp base is present in an amount of from about 5 wt % to about 80 wt %, based on the total weight of the composition. In a still further aspect, the hemp base is present in an amount of from about 5 wt % to about 60 wt %, based on the total weight of the composition. In yet a further aspect, the hemp base is present in an amount of from about 5 wt % to about 40 wt %, based on the total weight of the composition. In an even further aspect, the hemp base is present in an amount of from about 5 wt % to about 20 wt %, based on the total weight of the composition. In a further aspect, the hemp base is present in an amount of from about 10 wt % to about 98 wt %, based on the total weight of the composition. In a still further aspect, the hemp base is present in an amount of from about 20 wt % to about 98 wt %, based on the total weight of the composition. In yet a further aspect, the hemp base is present in an amount of from about 40 wt % to about 98 wt %, based on the total weight of the composition. In an even further aspect, the hemp base is present in an amount of from about 60 wt % to about 98 wt %, based on the total weight of the composition. In a still further aspect, the hemp base is present in an amount of from about 80 wt % to about 98 wt %, based on the total weight of the composition. In yet a further aspect, the hemp base is present in an amount of from about 20 wt % to about 80 wt %, based on the total weight of the composition. In an even further aspect, the hemp base is present in an amount of from about 40 wt % to about 60 wt %, based on the total weight of the composition. In various aspects, the hemp base is present in an amount of from about 10 wt % to about 90 wt %, based on the total weight of the composition. In various further aspects, the hemp base is present in an amount of from about 5 wt % to about 10 wt %, based on the total weight of the composition.

2. Particles

In one aspect, the disclosed cosmeceutical compositions comprise a hemp base, wherein the hemp base comprises a plurality of particles. Without wishing to be bound by theory, the plurality of particles can have a particle size range that is selected based on the end use of the desired cosmeceutical composition. For example, a particle size range of from about 1 micron to about 10 microns, from about 5 microns to about 25 microns, from about 10 microns to about 25 microns, from about 10 microns to about 100 microns, from about 25 microns to about 75 microns, from about 5 microns to about 50 microns, from about 50 microns to about 250 microns, from about 100 microns to about 250 microns, or from about 250 microns to about 1000 microns. Exemplary end uses of the disclosed cosmeceutical compositions include, but are not limited to, cleansers, moisturizers, toners, facial masks, sunscreens, exfoliants, foundations, concealers, blush, powders, bronzers, lip compositions (e.g., lip glosses, lipsticks, lip liners, etc.), eyeshadows, eyeliners, and mascaras.

Thus, in various aspects, the particles have a particle size range of from about 1 micron to about 10 microns. In a further aspect, the particles have a particle size range of from about 1 micron to about 8 microns. In a still further aspect, the particles have a particle size range of from about 1 micron to about 6 microns. In yet a further aspect, the particles have a particle size range of from about 1 micron to about 4 microns. In an even further aspect, the particles have a particle size range of from about 1 micron to about 2 microns. In a still further aspect, the particles have a particle size range of from about 2 micron to about 10 microns. In yet a further aspect, the particles have a particle size range of from about 4 micron to about 10 microns. In an even further aspect, the particles have a particle size range of from about 6 micron to about 10 microns. In a still further aspect, the particles have a particle size range of from about 8 micron to about 10 microns.

In various aspects, the particles have a particle size range of from about 10 microns to about 25 microns. In a further aspect, the particles have a particle size range of from about 10 microns to about 20 microns. In a still further aspect, the particles have a particle size range of from about 10 microns to about 15 microns. In yet a further aspect, the particles have a particle size range of from about 15 microns to about 25 microns. In an even further aspect, the particles have a particle size range of from about 20 microns to about 25 microns.

In various aspects, the particles have a particle size range of from about 25 microns to about 75 microns. In a further aspect, the particles have a particle size range of from about 25 microns to about 65 microns. In a still further aspect, the particles have a particle size range of from about 25 microns to about 55 microns. In yet a further aspect, the particles have a particle size range of from about 25 microns to about 45 microns. In an even further aspect, the particles have a particle size range of from about 25 microns to about 35 microns. In a still further aspect, the particles have a particle size range of from about 35 microns to about 75 microns. In yet a further aspect, the particles have a particle size range of from about 45 microns to about 75 microns. In an even further aspect, the particles have a particle size range of from about 55 microns to about 75 microns. In a still further aspect, the particles have a particle size range of from about 65 microns to about 75 microns.

In various aspects, the particles have a particle size range of from about 5 microns to about 50 microns. In a further aspect, the particles have a particle size range of from about 5 microns to about 40 microns. In a still further aspect, the particles have a particle size range of from about 5 microns to about 30 microns. In yet a further aspect, the particles have a particle size range of from about 5 microns to about 20 microns. In an even further aspect, the particles have a particle size range of from about 5 microns to about 10 microns. In a still further aspect, the particles have a particle size range of from about 10 microns to about 50 microns. In yet a further aspect, the particles have a particle size range of from about 20 microns to about 50 microns. In an even further aspect, the particles have a particle size range of from about 30 microns to about 50 microns. In a still further aspect, the particles have a particle size range of from about 40 microns to about 50 microns.

In various aspects, the particles have a particle size range of from about 100 microns to about 250 microns. In a further aspect, the particles have a particle size range of from about 100 microns to about 225 microns. In a still further aspect, the particles have a particle size range of from about 100 microns to about 200 microns. In yet a further aspect, the particles have a particle size range of from about 100 microns to about 175 microns. In an even further aspect, the particles have a particle size range of from about 100 microns to about 150 microns. In a still further aspect, the particles have a particle size range of from about 100 microns to about 125 microns. In yet a further aspect, the particles have a particle size range of from about 125 microns to about 250 microns. In an even further aspect, the particles have a particle size range of from about 150 microns to about 250 microns. In a still further aspect, the particles have a particle size range of from about 175 microns to about 250 microns. In yet a further aspect, the particles have a particle size range of from about 200 microns to about 250 microns. In an even further aspect, the particles have a particle size range of from about 225 microns to about 250 microns.

3. Hemp Composition

In one aspect, the disclosed cosmeceutical compositions comprise a hemp base, wherein the hemp base was produced from a hemp composition. In a further aspect, produced is via extraction. In a still further aspect, produced is via de-gumming.

In various aspects, the hemp base was produced via micronizing a hemp flour, wherein the hemp flour was produced via extraction from a hemp composition. In a further aspect, the hemp composition consists essentially of a hemp flour. Thus, in various aspects, the hemp composition comprises the hemp flour in an amount of at least about 75 wt %, at least about 80 wt %, at least about 85 wt %, at least about 90 wt %, at least about 95 wt %, at least about 99 wt %, or greater than about 99 wt %.

In various aspects, the hemp base was produced via micronizing a hemp flour, wherein the hemp flour was produced via de-gumming a hemp composition. In a further aspect, the hemp composition consists essentially of a hemp fiber. In a still further aspect, de-gumming is enzymatic de-gumming. Thus, in various aspects, the hemp composition comprises the hemp fiber in an amount of at least about 75 wt %, at least about 80 wt %, at least about 85 wt %, at least about 90 wt %, at least about 95 wt %, at least about 99 wt %, or greater than about 99 wt %.

In various aspects, the hemp composition is substantially free of cannabinoids. Cannabinoids are a class of diverse chemical compounds that act on cannabinoid receptors on cells that repress neurotransmitter release in the brain. Cannabinoid receptors are of a class of cell membrane receptors under the G protein-coupled receptor superfamily. As is typical of G protein-coupled receptors, the cannabinoid receptors contain seven transmembrane spanning domains. There are currently two known subtypes of cannabinoid receptors, termed CB1 and CB2, with mounting evidence of more. The CB1 receptor is expressed mainly in the brain (central nervous system), but also in the lungs, liver and kidneys. The CB2 receptor is expressed mainly in the immune system and in hematopoietic cells.

The classical cannabinoids are derived from their respective 2-carboxylic acids (2-COOH) by decarboxylation, catalyzed by heat, light, or alkaline conditions. Phyto-cannabinoids (those derived from the Cannabis plant) include but not limited to: tetrahydrocannabinol (THC), tetrahydrocannabinolic acid (THCA), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV) and cannabigerol monomethyl ether (CBGM).

Thus, in various aspects, the hemp composition comprises less than about 10 wt % cannabinoids. In a further aspect, the hemp composition comprises less than about 9 wt % cannabinoids. In a still further aspect, the hemp composition comprises less than about 8 wt % cannabinoids. In yet a further aspect, the hemp composition comprises less than about 7 wt % cannabinoids. In an even further aspect, the hemp composition comprises less than about 6 wt % cannabinoids. In a still further aspect, the hemp composition comprises less than about 5 wt % cannabinoids. In yet a further aspect, the hemp composition comprises less than about 4 wt % cannabinoids. In an even further aspect, the hemp composition comprises less than about 3 wt % cannabinoids. In a still further aspect, the hemp composition comprises less than about 2 wt % cannabinoids. In yet a further aspect, the hemp composition comprises less than about 1 wt % cannabinoids. In an even further aspect, the hemp composition comprises less than about 0.5 wt % cannabinoids. In a still further aspect, the hemp composition comprises less than about 0.1 wt % cannabinoids. In yet a further aspect, the hemp composition comprises less than about 0.05 wt % cannabinoids. In an even further aspect, the hemp composition comprises less than about 0.01 wt % cannabinoids.

C. Methods For Making a Hemp Base

In one aspect, disclosed are methods for making a hemp base having a plurality of particles within a particle size range, the method comprising: (a) micronizing a hemp flour consisting essentially of a hemp hurd or a hemp seed shell, thereby providing a particulate hemp composition; and (b) isolating the plurality of particles based on the particle size range, thereby producing the hemp base.

In one aspect, disclosed are methods for making a hemp base having a plurality of particles within a particle size range, the method comprising: (a) extracting from a hemp composition consisting essentially of a hemp flower, thereby producing a hemp flour comprising cellulose and lignin; (b) micronizing the hemp flour to provide a particulate hemp composition; and (c) isolating the plurality of particles based on the particle size range, thereby producing the hemp base.

In one aspect, disclosed are methods for making a hemp base having a plurality of particles within a particle size range, the method comprising: (a) de-gumming a hemp composition consisting essentially of a hemp fiber, thereby producing a hemp flour comprising cellulose and lignin; (b) micronizing the hemp flour to provide a particulate hemp composition; and (c) isolating the plurality of particles based on the particle size range, thereby producing the hemp base.

In various aspects, the hemp base is substantially free of oil.

In various aspects, the hemp base comprises less than about 10 wt % oil. In a further aspect, the hemp base comprises less than about 9 wt % oil. In a still further aspect, the hemp base comprises less than about 8 wt % oil. In yet a further aspect, the hemp base comprises less than about 7 wt % oil. In an even further aspect, the hemp base comprises less than about 6 wt % oil. In a still further aspect, the hemp base comprises less than about 5 wt % oil. In yet a further aspect, the hemp base comprises less than about 4 wt % oil. In an even further aspect, the hemp base comprises less than about 3 wt % oil. In a still further aspect, the hemp base comprises less than about 2 wt % oil. In yet a further aspect, the hemp base comprises less than about 1 wt % oil. In an even further aspect, the hemp base comprises less than about 0.5 wt % oil. In a still further aspect, the hemp base comprises less than about 0.1 wt % oil. In yet a further aspect, the hemp base comprises less than about 0.05 wt % oil. In an even further aspect, the hemp base comprises less than about 0.01 wt % oil.

In various aspects, the hemp base consists essentially of cellulose and lignin. Thus, in various aspects, the hemp base comprises the cellulose and/or lignin in an amount of at least about 75 wt %, at least about 80 wt %, at least about 85 wt %, at least about 90 wt %, at least about 95 wt %, at least about 99 wt %, or greater than about 99 wt %.

In various aspects, the particles have a particle size range of from about 1 micron to about 10 microns. In a further aspect, the particles have a particle size range of from about 1 micron to about 8 microns. In a still further aspect, the particles have a particle size range of from about 1 micron to about 6 microns. In yet a further aspect, the particles have a particle size range of from about 1 micron to about 4 microns. In an even further aspect, the particles have a particle size range of from about 1 micron to about 2 microns. In a still further aspect, the particles have a particle size range of from about 2 micron to about 10 microns. In yet a further aspect, the particles have a particle size range of from about 4 micron to about 10 microns. In an even further aspect, the particles have a particle size range of from about 6 micron to about 10 microns. In a still further aspect, the particles have a particle size range of from about 8 micron to about 10 microns.

In various aspects, the particles have a particle size range of from about 10 microns to about 25 microns. In a further aspect, the particles have a particle size range of from about 10 microns to about 20 microns. In a still further aspect, the particles have a particle size range of from about 10 microns to about 15 microns. In yet a further aspect, the particles have a particle size range of from about 15 microns to about 25 microns. In an even further aspect, the particles have a particle size range of from about 20 microns to about 25 microns.

In various aspects, the particles have a particle size range of from about 25 microns to about 75 microns. In a further aspect, the particles have a particle size range of from about 25 microns to about 65 microns. In a still further aspect, the particles have a particle size range of from about 25 microns to about 55 microns. In yet a further aspect, the particles have a particle size range of from about 25 microns to about 45 microns. In an even further aspect, the particles have a particle size range of from about 25 microns to about 35 microns. In a still further aspect, the particles have a particle size range of from about 35 microns to about 75 microns. In yet a further aspect, the particles have a particle size range of from about 45 microns to about 75 microns. In an even further aspect, the particles have a particle size range of from about 55 microns to about 75 microns. In a still further aspect, the particles have a particle size range of from about 65 microns to about 75 microns.

In various aspects, the particles have a particle size range of from about 5 microns to about 50 microns. In a further aspect, the particles have a particle size range of from about 5 microns to about 40 microns. In a still further aspect, the particles have a particle size range of from about 5 microns to about 30 microns. In yet a further aspect, the particles have a particle size range of from about 5 microns to about 20 microns. In an even further aspect, the particles have a particle size range of from about 5 microns to about 10 microns. In a still further aspect, the particles have a particle size range of from about 10 microns to about 50 microns. In yet a further aspect, the particles have a particle size range of from about 20 microns to about 50 microns. In an even further aspect, the particles have a particle size range of from about 30 microns to about 50 microns. In a still further aspect, the particles have a particle size range of from about 40 microns to about 50 microns.

In various aspects, the particles have a particle size range of from about 100 microns to about 250 microns. In a further aspect, the particles have a particle size range of from about 100 microns to about 225 microns. In a still further aspect, the particles have a particle size range of from about 100 microns to about 200 microns. In yet a further aspect, the particles have a particle size range of from about 100 microns to about 175 microns. In an even further aspect, the particles have a particle size range of from about 100 microns to about 150 microns. In a still further aspect, the particles have a particle size range of from about 100 microns to about 125 microns. In yet a further aspect, the particles have a particle size range of from about 125 microns to about 250 microns. In an even further aspect, the particles have a particle size range of from about 150 microns to about 250 microns. In a still further aspect, the particles have a particle size range of from about 175 microns to about 250 microns. In yet a further aspect, the particles have a particle size range of from about 200 microns to about 250 microns. In an even further aspect, the particles have a particle size range of from about 225 microns to about 250 microns.

In a further aspect, extracting is via single solvent extraction, superfluid extraction, gas extraction, or steam extraction. In a still further aspect, extracting is via single solvent extraction. In yet a further aspect, extracting is via superfluid extraction. In an even further aspect, extracting is via gas extraction. In a still further aspect, extracting is via steam extraction.

In a further aspect, extracting is with a solvent selected from water and an alcohol.

In a still further aspect, extracting is with water. In yet a further aspect, extracting is with an alcohol. In an even further aspect, extracting is with both water and an alcohol.

In a further aspect, micronizing is milling.

In a further aspect, de-gumming is enzymatic de-gumming.

In a further aspect, the particulate hemp composition has an average particle size of at least about 5 microns.

In a further aspect, the method further comprises combining the hemp base with one or more additives. Examples of additives include, but are not limited to, a colorant, an emollient, a flavorant, a fragrant, a sunscreen, a self-tanning agent, an opacifying agent, a moisturizer, a film former, a thickening agent, a conditioning agent, a deodorant, an emulsifier, a humectant, a softener, a lubricant, a penetrant, a plastisizer, a dispersant, a preservative, and mixtures thereof.

In a further aspect, the additive is present in an amount of from about 0.01 wt % to about 10 wt % of the composition. In a still further aspect, the additive is present in an amount of from about 0.01 wt % to about 8 wt % of the composition. In yet a further aspect, the additive is present in an amount of from about 0.01 wt % to about 6 wt % of the composition. In an even further aspect, the additive is present in an amount of from about 0.01 wt % to about 4 wt % of the composition. In a still further aspect, the additive is present in an amount of from about 0.01 wt % to about 2 wt % of the composition. In yet a further aspect, the additive is present in an amount of from about 0.01 wt % to about 1 wt % of the composition. In an even further aspect, the additive is present in an amount of from about 0.1 wt % to about 10 wt % of the composition. In a still further aspect, the additive is present in an amount of from about 1 wt % to about 10 wt % of the composition. In yet a further aspect, the additive is present in an amount of from about 2 wt % to about 10 wt % of the composition. In an even further aspect, the additive is present in an amount of from about 4 wt % to about 10 wt % of the composition. In a still further aspect, the additive is present in an amount of from about 6 wt % to about 10 wt % of the composition. In yet a further aspect, the additive is present in an amount of from about 8 wt % to about 10 wt % of the composition.

The previous description of the disclosed aspects is provided to enable any person skilled in the art to make or use the present disclosure. Various modifications to these aspects will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A cosmeceutical composition comprising a hemp base derived solely from a hemp hurd and/or hemp seed shell,
   wherein the hemp base comprises a plurality of particles,
   wherein the hemp base comprises cellulose and/or lignin in an amount of at least about 95 wt % and less than about 1 wt % oil,
   wherein the hemp base is produced by a method comprising micronizing a hemp flour comprising a hemp hurd and/or a hemp seed shell in an amount of at least about 95 wt %, and
   wherein the method does not include an extracting or de-gumming step.

2. The composition of claim 1, wherein the hemp base is present in an amount of from about 10 wt % to about 90 wt %, based on the total weight of the composition.

3. The composition of claim 1, wherein the particles have a particle size range of from about 1 micron to about 10 microns.

4. The composition of claim 1, wherein the particles have a particle size range of from about 10 microns to about 25 microns.

5. The composition of claim 1, wherein the particles have a particle size range of from about 25 microns to about 75 microns.

6. The composition of claim 1, wherein the particles have a particle size range of from about 5 microns to about 50 microns.

7. The composition of claim 1, wherein the particles have a particle size range of from about 100 microns to about 250 microns.

8. A cosmeceutical composition comprising a hemp base derived solely from a hemp hurd and/or hemp seed shell,
   wherein the hemp base has a plurality of particles within a particle size range, wherein the hemp base comprises cellulose and/or lignin in an amount of at least about 99 wt % and less than 0.05 wt % oil, and wherein the hemp base was produced by a method comprising:
(a) micronizing a hemp flour comprising a hemp hurd and/or a hemp seed shell in an amount of at least about 99 wt %; and
(b) isolating the plurality of particles based on the particle size range, wherein the method does not include an extracting or de-gumming step.

9. The composition of claim 8, wherein the hemp base is present in an amount of from about 10 wt % to about 90 wt %, based on the total weight of the composition.

10. The composition of claim 1, wherein the composition is a topical composition.

11. The composition of claim 10, wherein the composition is formulated as a cream.

12. The composition of claim 8, wherein the composition is a topical composition.

13. The composition of claim 12, wherein the composition is formulated as a cream.

14. The composition of claim 1, wherein the hemp base comprises cellulose and/or lignin in an amount of at least about 99 wt %.

15. The composition of claim 1, wherein the hemp base comprises less than 0.05 wt % oil.

16. The composition of claim 1, wherein the hemp flour comprises a hemp hurd and/or a hemp seed shell in an amount of at least about 99 wt %.

17. The composition of claim 8, wherein the particles have a particle size range of from about 1 micron to about 10 microns.

18. The composition of claim 8, wherein the particles have a particle size range of from about 10 microns to about 25 microns.

19. The composition of claim 8, wherein the particles have a particle size range of from about 25 microns to about 75 microns.

20. The composition of claim 8, wherein the particles have a particle size range of from about 5 microns to about 50 microns.

* * * * *